Jan. 16, 1973 C. H. SAURET Plant Pat. 3,293
ALMOND TREE
Filed June 7, 1971
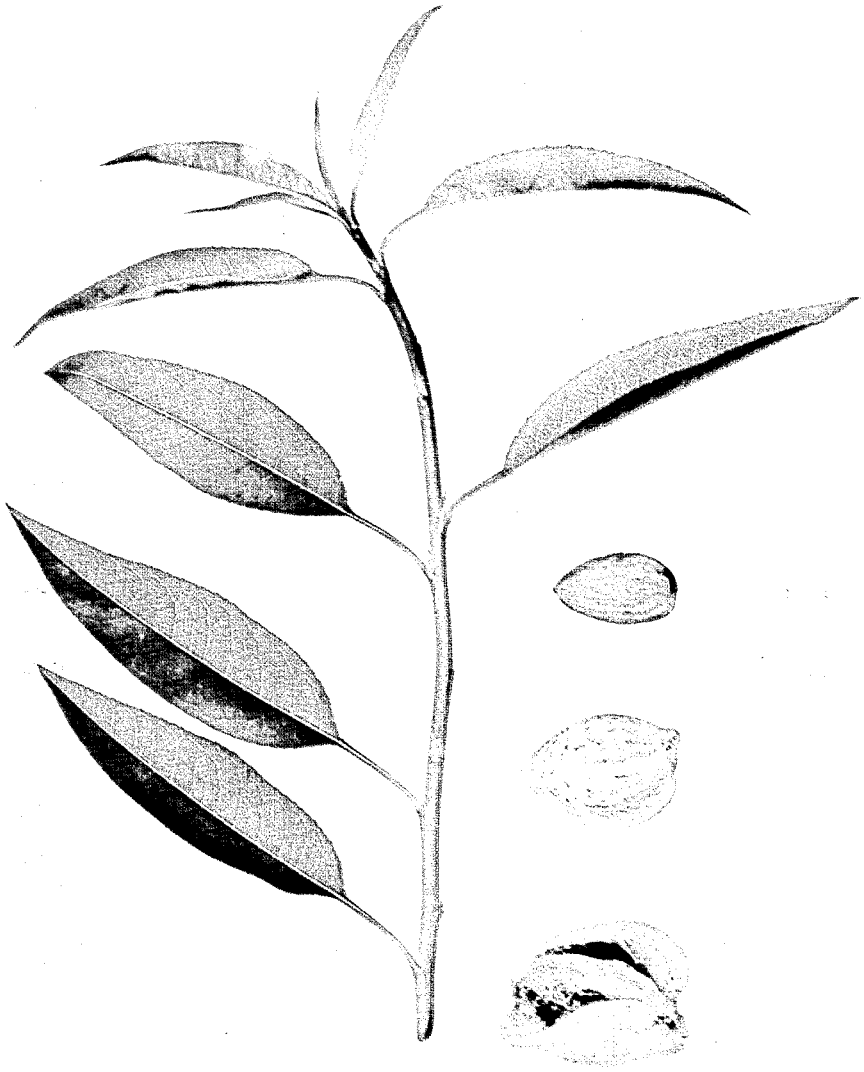
INVENTOR
Clarence H. Sauret
BY
Webster & Webster
ATTORNEYS

United States Patent Office

Plant Pat. 3,293
Patented Jan. 16, 1973

3,293

ALMOND TREE

Clarence H. Sauret, Paso Robles, Calif., assignor of a fractional part interest to Richard K. Sauret, Paso Robles, Calif.

Filed June 7, 1971, Ser. No. 150,855
Int. Cl. A01h *5/03*
U.S. Cl. Plt.—30 1 Claim

ABSTRACT OF THE DISCLOSURE

An almond tree characterized by large size, vigorous growth, medium density, abundant foliage with medium-size ovate leaves, and regular and heavy production of small, well-distributed nuts easy to harvest, hull, and process; the variety blooming, pollinating, and harvesting with the Nonpareil (unpatented); the nuts, of good quality and good flavor, averaging 370 per pound; the percentage of kernel to nut averaging 66%; and the kernels averaging 35.5 per ounce.

ORIGIN OF THE VARIETY

The present variety of almond tree was discovered by me growing as a chance seedling in an orchard—of which at the time of such discovery I was an owner—located in the Oak Flat area of San Luis Obispo County, Calif. When such seedling (which I maintained under close and continuing observation) matured and bore a crop, I recognized that it had certain new and distinctive characteristics which made the variety desirable for commercial growing.

ASEXUAL REPRODUCTION OF THE VARIETY

After my discovery of the variety as a chance seedling, and recognition by me of its desirable characteristics, I asexually reproduced the variety by grafting on mature Davey (unpatented) trees in the aforementioned orchard. In maturity, such reproductions ran true to the parent tree in all respects.

SUMMARY OF THE VARIETY

The herein claimed almond tree provides a commercially desirable variety which blooms, pollinates, and harvests with the Nonpareil, while being particularly characterized, as to novelty, by the regular and heavy production of small, well-distributed nuts of good quality and good flavor, which are easy to harvest, hull, and process; the small nuts being relatively high in average number per pound, average percentage of kernel to nut, and average number of kernels per ounce.

The herein claimed almond tree is further characterized by a tree of large size, vigorous growth, medium density, and abundant foliage with medium-size ovate leaves.

BRIEF DESCRIPTION OF THE DRAWING

The drawing is an illustration, by photographic reproduction in color, of a twig with leaves, a nut in hull, a nut out of hull, and a separate kernel.

DESCRIPTION OF THE VARIETY

The botanical details of this new and distinct variety of almond tree—with color definitions in common color terms—are as follows:

Tree:
- *Size.*—Large.
- *Density.*—Medium.
- *Vigor.*—Vigorous.

Trunk: Form—average.

Branches:
- *Form.*—Medium.
- *Texture.*—Smooth.
- *Branching habit.*—Upright.
- *Lenticels.*—Large, medium number.

Foliage: Quantity—abundant.

Leaves:
- *Size.*—Medium; average length—68 mm.; average width—27 mm.
- *Shape.*—Ovate.
- *Thickness.*—Medium.
- *Texture.*—Smooth.
- *Margin.*—Similar to Nonpareil, but ridge not as jagged.
- *Petiole.*—Medium.
- *Glands.*—Average number—2 to 3; alternate; average size.
- *Color.*—Dark green, slightly lighter on new growth.

Bloom:
- *Amount of bloom.*—Heavy.
- *Color.*—White.
- *Blooming period.*—With Nonpareil; spans 25 to 30 days.

Crop:
- *Bearing.*—Regular bearer.
- *Productivity.*—Heavy.
- *Distribution of nuts on tree.*—Well distributed.
- *Harvest period.*—With Nonpareil.
- *Tenacity.*—Hangs well on tree; easy to harvest; easy to process.

Hull:
- *Outer surface.*—Medium.
- *Form.*—Regular.
- *Thickness.*—Thin.
- *Flesh.*—Medium tough.
- *Suture.*—Ridged.
- *Color at harvest.*—Yellow to red.
- *Dehiscence.*—Wide.
- *Splitting.*—Along suture.

Nut:
- *Size.*—Small—average length — 32 mm.; average width—25 mm.; average thickness—20 mm.; nuts (in shell) per pound on average sample—370.
- *Form.* — Length/width — ovate. Width/thickness—medium.
- *Shell.*—Thin; ragged. Outer shell—crumbly. Inner shell—medium to soft well sealed.
- *Color.*—Brown.
- *Pits.*—Small; irregular.
- *Base.*—Ventrally oblique.
- *Stem scar.*—Large.
- *Apex.*—Very sharp.
- *Wing.*—Thin; wide.
- *Inner surface.*—Light.
- *Ventral streak.*—Light; broad; long.
- *Percentage of kernel to nut on average sample.*—66%.

Kernel:
- *Size.* — Small; average length — 23 mm.; average width—14 mm.; average thickness—11 mm.
- *Kernels per ounce on average sample.*—35.5
- *Form.* — Length/width — ovate. Width/thickness—medium.
- *Base.*—Ventrally oblique.
- *Stem scar.*—Small.
- *Apex.*—Rounded; sharp.
- *Surface.*—Moderately smooth.
- *Pellicle.*—Moderately thick.
- *Pubescence.*—None.
- *Color.*—Brown.
- *Number of doubles.*—Very few.

*Defective kernels.*—Very rarely.
*Deformed kernels.*—Very rarely.
*Flavor.*—Good.
*Quality.*—Good.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, which is of large size, vigorous in growth, of medium density, abundant of foliage with medium-size ovate leaves, and a regular and heavy producer of small well-distributed nuts easy to harvest, hull, and process; the variety blooming, pollinating, and harvesting with the Nonpareil; the nuts, of good quality and good flavor, being relatively high in average number per pound, average percentage of kernel to nut, and average number of kernels per ounce.

No references cited.

ROBERT E. BAGWILL, Primary Examiner